(12) United States Patent
Persat

(10) Patent No.: US 8,622,977 B2
(45) Date of Patent: Jan. 7, 2014

(54) CARRIER FOR INJECTING A PRODUCT INTO THE HUMAN BODY

(76) Inventor: Jean-Charles Persat, Collex-Bossy (CH)

(*) Notice: Subject to any disclaimer, the term of this patent is extended or adjusted under 35 U.S.C. 154(b) by 65 days.

(21) Appl. No.: 13/203,250

(22) PCT Filed: Feb. 25, 2010

(86) PCT No.: PCT/FR2010/050326
§ 371 (c)(1),
(2), (4) Date: Oct. 24, 2011

(87) PCT Pub. No.: WO2010/097551
PCT Pub. Date: Sep. 2, 2010

(65) Prior Publication Data
US 2012/0035551 A1    Feb. 9, 2012

(30) Foreign Application Priority Data
Feb. 25, 2009   (FR) ...................................... 09 51194

(51) Int. Cl.
*A61M 5/00* (2006.01)
*A61M 5/31* (2006.01)
*A61M 25/00* (2006.01)
*A61M 5/32* (2006.01)

(52) U.S. Cl.
USPC ............................ 604/239; 604/264; 604/274

(58) Field of Classification Search
USPC ................. 604/239, 240, 243, 264, 272–274, 604/411–412
See application file for complete search history.

(56) References Cited

U.S. PATENT DOCUMENTS

| 2,634,726 A | 4/1953 | Hanson |
| 4,413,993 A | 11/1983 | Guttman |
| 5,718,677 A * | 2/1998 | Capetan et al. ................. 604/35 |
| 5,919,170 A | 7/1999 | Woessner |
| 6,074,371 A | 6/2000 | Fischell |
| 2005/0192560 A1 | 9/2005 | Walls et al. |
| 2010/0280498 A1 * | 11/2010 | Olsen ........................... 604/544 |

FOREIGN PATENT DOCUMENTS

| DE | 94 00 470 | 3/1983 |
| FR | 2 808 208 | 11/2001 |
| WO | 01/97743 | 12/2001 |
| WO | 2008/155145 | 12/2008 |

* cited by examiner

*Primary Examiner* — Nicholas Lucchesi
*Assistant Examiner* — Rebecca E Eisenberg
(74) *Attorney, Agent, or Firm* — Clark & Brody

(57) ABSTRACT

The invention relates to a carrier for injecting a filler product, in particular for microplasty or lipo-reconstruction, comprising a semi-rigid tubular needle (2) having a longitudinal axis with a closed hemispherical distal end and a proximal end (3) for connecting to an injection device, said needle having an inner tubular surface defining an inner transverse cross-section and an outer tubular surface defining an outer transverse cross-section, wherein at least one output side opening (11) is formed in the needle in the vicinity of the distal end. According to the invention, at least one output side opening (11) is defined by a peripheral edge (12) with a rounded connection profile free of any protruding edge, between the inner and outer surfaces of the needle, and the wall of the needle (1) has a thickness, from the proximal end (3) and over a predetermined length of the needle, which is greater than the thickness of the needle which is constant up to the distal end.

10 Claims, 1 Drawing Sheet

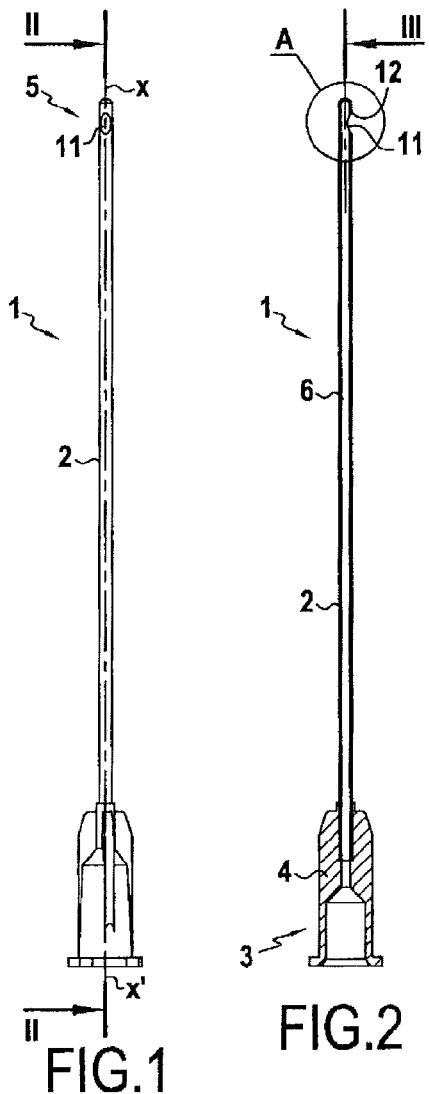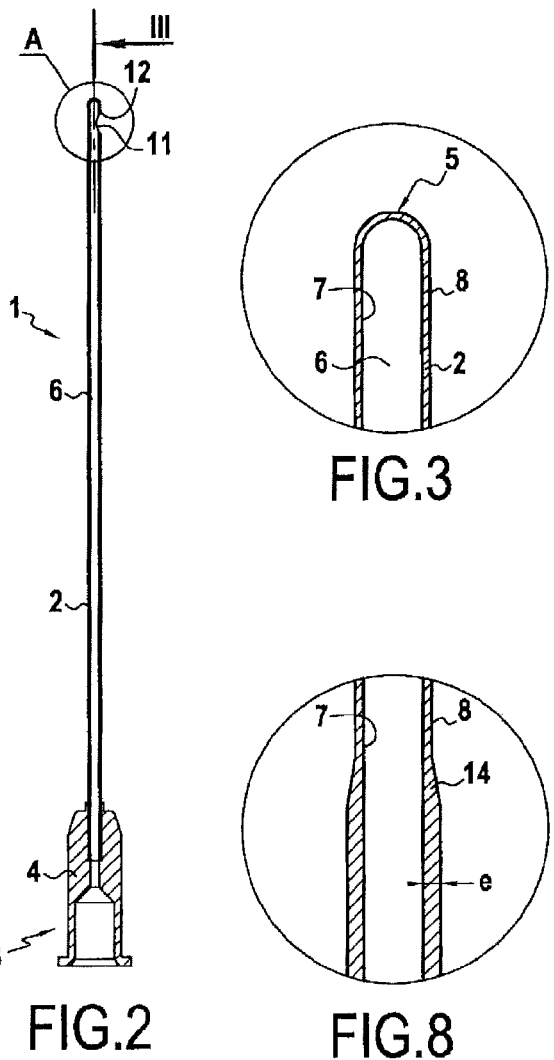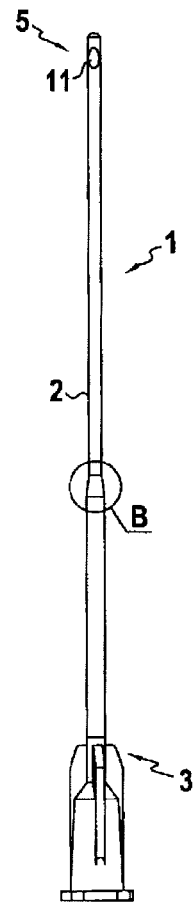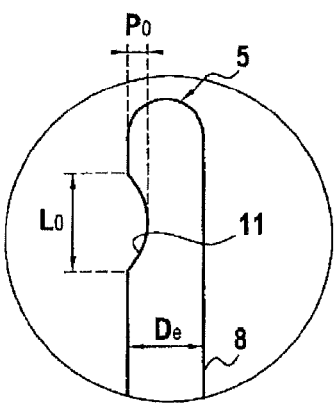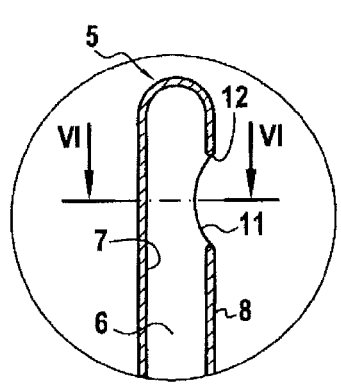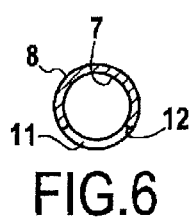

CARRIER FOR INJECTING A PRODUCT INTO THE HUMAN BODY

The present invention relates to the general technical field of carriers for injecting a product into the human body, and it more specifically targets the injection carriers used in the field of non-invasive transcutaneous cosmetic surgery.

This cosmetic surgery technique consists of repairing cutaneous cosmetic flaws in the look, silhouette, contour of the face and body in general. The treatment technique consists of reducing the cosmetic flaws by filling in different cutaneous, subcutaneous, muscular and periosseous layers, either through autologous grafting of the patient's own adipocytes (fat cells taken from the anatomical sites richest in fat), or by the injection and infiltration of the tissue spaces by a synthetic filler product such as hyaluronic acid, which takes the form of a hydrophilic gel with different levels of viscosity.

In the state of the art, it is known, to inject a filler product, to use straight cannulas called Coleman's cannulas to proceed with the injections at the desired locations. The use of such cannulas causes a certain number of drawbacks, such as the appearance of pains and tearing of the cutaneous muscles.

To try to provide a solution to the use of these cannulas, in particular in the field of facial reconstruction, patent FR 2 808 208 proposed a set of cannulas for injections implementing three cannulas with distinct geometric configurations adapted to the different parts of the face. In general, each cannula includes a semi-rigid tubular needle having a closed hemispherical distal end and a proximal end for connecting to an injection device. This needle also has an output side opening arranged near the distal end. Although these cannulas have an atraumatic foam end, multiple tissue traumas have been observed with a multiple risk of infections, micro-lesions, cutaneous micro-hematomas that can leave unsightly and permanent sequellae (in the form of hemorrhagic stippling with micro-mematoma marks). Moreover, the injection with such a cannula leads to the irregular injection of the product, which spreads in the shape of a string of beads. This result is unsightly and requires a local massage after injection to try to eliminate its impact. Over-consumption of the injected product should also be noted due to the formation of the string with large drops of product. This cannula is also fragile, making it delicate to use.

In the state of the art, also known are hypodermic needles designed to ensure a deep injection. For example, U.S. Pat. No. 2,634,726 describes a hypodermic needle having a beveled end and a curved output side opening. Likewise, document DE 94 00 470 U1 also describes a hypodermic needle including a beveled end and a decrease in cross-section opposite the output side opening. U.S. Pat. No. 4,413,993 describes a needle for intravenous injection having a beveled end. All of these needles are not adapted for the field of non-invasive transcutaneous cosmetic surgery.

In the state of the art, also known are urinary catheters, in particular from documents US 2005/0192560, U.S. Pat. No. 5,919,170 and WO 2008-155145. These catheters include a tube whereof one distal end is rounded and upstream of which a passage opening is formed. Such catheters are not adapted to serve as an atraumatic carrier for transcutaneously injecting a product with a regular flow.

The object of the invention therefore aims to resolve the aforementioned drawbacks by proposing an injection carrier for microplasty or lipo-reconstruction, with a robust and safe construction, ensuring a regular flow of the injected product and the use of which is atraumatic and does not lead to the appearance of pain and hematomas in patients.

To achieve such an aim, the object of the invention relates to a carrier for injecting a filler product, in particular for microplasty or lipo-reconstruction, comprising a semi-rigid tubular needle having a longitudinal axis with a closed hemispherical distal end and a proximal end for connecting to an injection device, said needle having an inner tubular surface defining an inner transverse cross-section and an outer tubular surface defining an outer transverse cross-section, wherein at least one output side opening is formed in the needle in the vicinity of the distal end.

According to the invention, at least one output side opening is defined by a peripheral edge with a rounded connection profile free of any protruding edge, between the inner and outer surfaces of the needle, and the wall of the needle has a thickness, from the proximal end and over a predetermined length of the needle, which is greater than the thickness of the needle which is constant up to the distal end.

Furthermore, the injection carrier according to the invention can include, in combination, at least one and/or another of the following additional features:
- the tubular needle has, over substantially one third of its length starting from the proximal end, a wall with a thickness that is substantially twice the thickness of the rest of the needle up to the distal end,
- the tubular needle has a gradual connecting zone between the thicknesses of the wall of the needle,
- the output side opening has a surface such that $Si < So$, $5 Si$, with $Si$ equal to the surface of the inner transverse cross-section of the needle,
- the output side opening has a radial depth such that $Po \leq De/1.7$, with $De$ the diameter of the outer face of the needle,
- the output side opening has a length taken substantially parallel to the longitudinal axis of the needle, such that $De < Lo < 2.5 De$, with $De$ the diameter of the outer face of the needle,
- the needle has an outer diameter between 0.15 and 1 mm and preferably between 0.4 and 0.9 mm,
- the needle has a length between 2 and 15 cm and preferably between 4 and 10 cm.

Various other features will emerge from the description provided below in reference to the appended drawings that show, as non-limiting examples, embodiments of the object of the invention.

FIG. 1 is a front view of one example of an embodiment of an injection carrier according to the invention.

FIG. 2 is a cross-sectional elevation view considered substantially along lines II-II of FIG. 1.

FIG. 3 is a partial cross-section taken substantially along line III of FIG. 2.

FIG. 4 is a cross-sectional view of a detail "A" of the injection carrier illustrated in FIG. 2.

FIG. 5 is a larger-scale side view of detail "A" of the distal end of the injection carrier illustrated in FIG. 2.

FIG. 6 is a transverse cross-sectional view taken substantially along lines VI-VI of FIG. 4.

FIG. 7 is a view of another example embodiment of an injection carrier according to the invention.

FIG. 8 is a larger-scale view of a detail "B" of the injection carrier illustrated in FIG. 7.

As emerges more precisely from FIGS. 1 and 2, the object of the invention relates to an injection carrier 1 such as a cannula or a needle within the general meaning adapted to inject (or remove?) a filler product within the general meaning in the human body in the field of cosmetic surgery such as for microplasty or lipo-reconstruction. For example, the injection carrier 1 makes it possible to inject, for microplasty, hyaluronic acid or any other filler substance, and for lipo-reconstruction, autologous fat.

This injection carrier 1 includes a semi-rigid tubular needle 2 having a longitudinal axis of symmetry xx'. Advantageously, this tubular needle 2 is made from a metal material such as stainless steel. This tubular needle 2 has a proximal end 3 for connecting to an injection device (not shown), such as a syringe. Traditionally, this proximal end 3 is provided with an adaptor tip 4, for example of the "Luer lock" type.

This tubular needle 2 has, opposite the proximal end 3, a closed rounded or hemispherical distal end 5 as emerges clearly from FIG. 3. The tubular needle 2 thus has a so-called atraumatic foam end.

This tubular needle 2 has an inner channel 6 defined by a tubular inner face 7 having an inner transverse cross-section Si. This tubular needle 2 has a tubular outer face 8 defining an outer transverse cross-section Se. Preferably, the inner transverse cross-section Si of the tubular needle 2 is circular. Likewise, the outer transverse cross-section Se is circular.

The tubular needle 2 thus has a wall with a constant thickness e over part of its length, from the hemispherical distal end 5. The tubular needle 2 is made from a single metal mass so that no discontinuity or joint appears between the hemispherical distal end 5 and the tubular part of the needle. Thus, the wall of the hemispherical distal end 5 and the tubular needle over part of its length has a thickness e with a constant value.

As emerges more precisely from FIGS. 4 to 6, at least one output side opening 11 is arranged in the tubular needle 2 near the distal end 5. The tubular needle 2 has, from said output lateral opening 11 and going towards the distal end 5, an outer transverse cross-section with a constant value over the entire length of the tubular part of the needle and that decreases for the rounded distal end 5.

This output side opening 11 thus emerges on the inner 7 and outer 8 faces of the tubular needle 2, thereby allowing communication between the inner channel 6 and the outside of the needle. Traditionally, this side opening 11 provides the output of the filler product coming from the inner channel 6 and introduced using an injection device.

This output side opening 11 is defined over its entire perimeter by a peripheral edge 12 that, as appears clearly in FIGS. 4 and 6, has a rounded connection profile between the inner 7 and outer 8 faces of the needle. In other words, the peripheral edge 12 is free of any protruding edge between the inner 7 and outer 8 faces of the needle. The peripheral edge 12 thus has a rounded or convex profile along the entire circumference of the output side opening 11. It should be noted that the hemispherical distal end 5 associated with the output side opening 11 are completely atraumatic.

The output side opening 11 is thus completely blunt over its perimeter and does not have any metal unevenness or fins. This surface condition makes it possible to reduce abrasion of the tissues creating bleeding and pain. Likewise, the continuity of the surface of the tubular inner face 7 with the edge 12 of the output side opening 11 allows a laminar flow of the filler product without a risk of emulsifying the filler product at the profile break connected to the output side opening 11. Furthermore, this surface continuity or regularity of the tubular inner face 7 participates in automatically regulating the flow rate of the filler product, due to its high hydrodynamic resistance and due to the adjustment of this resistance by precise proportions between the section of the inner channel 6 and the section of the output side opening 11, as will be explained in the continuation of the description.

According to one advantageous feature, the output side opening 11 has a surface So such that Si<So<5 Si with Si equal to the surface of the inner transverse cross-section of the needle. The surface So of the output side opening 11 corresponds to the surface of the orifice that follows the profile or the tubular shape of the needle, and more precisely of the face 7, 8.

According to another advantageous feature, the output side opening 11 has a radial depth Po such that Po≤De/1.7, with De the diameter of the outer tubular face 8 of the needle.

According to another advantageous feature, the output side opening 11 has a length Lo taken along the longitudinal axis x, x' of the needle such that De<Lo<2.5 De, with De the diameter of the outer tubular face 8 of the needle.

It must be considered that the dimensions of the tubular needle 2 relative to the output side opening 11 make it possible to adjust the flow rate of the filler product so as to obtain a regular and homogenous flow rate combined with the rounded profile of the edge 12 of the output side opening 11. The tubular needle 2 thus has controlled hydrodynamic qualities making it possible to adjust the beginning of the filler product as a function of its viscosity. The use of a tubular needle 2 according to the invention prevents the irregular injection of the filler product in the form of a string of beads. Mastering all of these characteristics makes it possible to have a needle offering very good effectiveness for each filler product and each specialized gesture performed and in particular for the most critical ones concerning in particular treatments for the face, under-eye shadows, forehead and cheekbones.

In a complementary manner, the injection carrier 1 is miniaturized, making it possible to pass below the threshold for painful reactions of the cutaneous nerve endings. As a result, the treatments done using the injection carrier 1 according to the invention are painless.

According to one preferred application, the needle has an outer diameter De between 0.15 and 1 mm, and preferably between 0.4 and 0.9 mm.

According to one embodiment, the needle has a length between 2 and 15 cm and preferably between 4 and 10 cm.

It should be noted that the wall of the needle has a variable thickness e so as to adapt to the mechanical characteristics and constraints as well as surgical needs. FIGS. 7 and 8 illustrate one example embodiment in which the wall of the tubular needle 2 has a variable thickness. According to this example, the wall of the tubular needle 2 has a thickness e that varies by levels and increases going towards the proximal end 3 of the needle. Thus, the wall of the tubular needle 2 has a constant thickness over a first part of the tubular needle starting from the distal end 5 and a constant thickness greater than the thickness of the first portion, over a second part of the tubular needle up to the proximal end 5 of the tubular needle 2. For example, over one third of the length of the tubular needle 2 starting from the proximal end 3, the tubular needle 2 has a thickness e that is substantially twice the thickness of the rest of the needle up to the distal end 5. As emerges more precisely from FIG. 8, the tubular needle 2 has a gradual connection zone 14 between the two parts of the tubular needle 2 with different thicknesses, this gradual connection zone 14 extending over a limited length of the tubular needle 2. It should be noted that preferably, the diameter of the tubular inner face 7 remains constant whereas the diameter of the tubular outer face 8 varies.

The tubular needle 2 thus has mechanical characteristics such as suppleness, flexibility, mechanical strength, adapted to the constraints and needs of surgery. The stiffening sheathing of the tubular needle 2 from its proximal end 3 makes it possible to withstand splitting of the tissues without a risk of breakage of the tubular needle 2 given its small size.

The invention is not limited to the examples described and shown, as various changes can be made to it without going beyond the scope thereof.

The invention claimed is:

1. A carrier for injecting a filler product, in particular for microplasty or lipo-reconstruction, comprising a semi-rigid tubular needle (2) having a longitudinal axis with a closed hemispherical distal end (5) and a proximal end (3) for connecting to an injection device, said needle having an inner tubular surface (7) defining an inner transverse cross-section (Si) and an outer tubular surface (8) defining an outer transverse cross-section (Se), wherein at least one output side opening (11) is formed in the needle in the vicinity of the distal end, characterized in that at least one output side opening (11) is defined by a peripheral edge (12) with a rounded connection profile free of any protruding edge, between the inner and outer surfaces of the needle, and in that the wall of the needle (1) has a thickness (e), from the proximal end (3) and over a predetermined length of the needle, which is greater than the thickness of the needle which is constant up to the distal end (5), wherein the tubular needle is made from a single metal mass so that no discontinuity appears between the hemispherical distal end (5) and the tubular part of the needle.

2. An injection carrier according to claim 1, characterized in that the tubular needle (2) has, over substantially one third of its length starting from the proximal end (3), a wall with a thickness (e) that is substantially twice the thickness (e) of the rest of the needle up to the distal end (5).

3. The injection carrier according to claim 1, characterized in that the tubular needle (2) has a gradual connecting zone between the thicknesses of the wall of the needle.

4. The injection carrier according to claim 1, characterized in that the output side opening (11) has a surface (So) such that $Si<So\leq 5\,Si$, with Si equal to the surface of the inner transverse cross-section of the needle.

5. The injection carrier according to claim 4, characterized in that the output side opening (11) has a radial depth (Po) such that $Po\leq De/1.7$, with De the diameter of the outer face (8) of the needle.

6. The injection carrier according to claim 4, characterized in that the output side opening (11) has a length (Lo) taken substantially parallel to the longitudinal axis of the needle, such that $De<Lo<2.5\,De$, with De the diameter of the outer face (8) of the needle.

7. The injection carrier according to claim 1, characterized in that the needle (2) has an outer diameter (De) between 0.15 and 1 mm.

8. The injection carrier according to claim 7, characterized in that the needle (2) has an outer diameter (De) between 0.4 and 0.9 mm.

9. The injection carrier according to claim 1, characterized in that the needle (2) has a length between 2 and 15 cm.

10. The injection carrier according to claim 9, characterized in that the needle (2) has a length between 4 and 10 cm.

* * * * *

UNITED STATES PATENT AND TRADEMARK OFFICE
CERTIFICATE OF CORRECTION

PATENT NO.         : 8,622,977 B2                                        Page 1 of 1
APPLICATION NO.    : 13/203250
DATED              : January 7, 2014
INVENTOR(S)        : Jean-Charles Persat It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 97 days.

Signed and Sealed this

Twenty-second Day of September, 2015

Michelle K. Lee
*Director of the United States Patent and Trademark Office*